United States Patent [19]

Berger

[11] Patent Number: 4,808,171
[45] Date of Patent: Feb. 28, 1989

[54] V-SHAPED EAR VENTILATION TUBE

[76] Inventor: Eric S. Berger, 2025 W. 6th St., Aberdeen, Wash. 98520

[21] Appl. No.: 864,080

[22] Filed: May 16, 1986

[51] Int. Cl.$^4$ ............................................. A61M 5/325
[52] U.S. Cl. ..................................................... 604/264
[58] Field of Search ................... 128/151, 152, 350 R, 128/1 R, 343, 200.26; 623/10; 604/264, 26, 175

[56] References Cited
U.S. PATENT DOCUMENTS 3,948,271 4/1976 Akiyama ............................ 604/264
4,094,303 6/1978 Johnston .............................. 623/10

*Primary Examiner*—John D. Yasko
*Attorney, Agent, or Firm*—Pravel, Gambrell, Hewitt, Kimball & Krieger

[57] ABSTRACT

An ear ventilation tube adapted for insertion in the tympanic membrane of the ear for communicating fluid between the middle and outer ear formed by two conical body portions joined at their narrow ends with an opening through the center of the conical flanges for the passage of fluid. The outer surface of the ventilation tube forms a V-shape with the restricted portion near the center of the ventilation tube. The inner surface of the ventilation tube along the opening has a middle restricted portion and two end portions of significantly larger size in order to enhance the flow of fluid through the opening.

5 Claims, 1 Drawing Sheet

U.S. Patent  Feb. 28, 1989  4,808,171
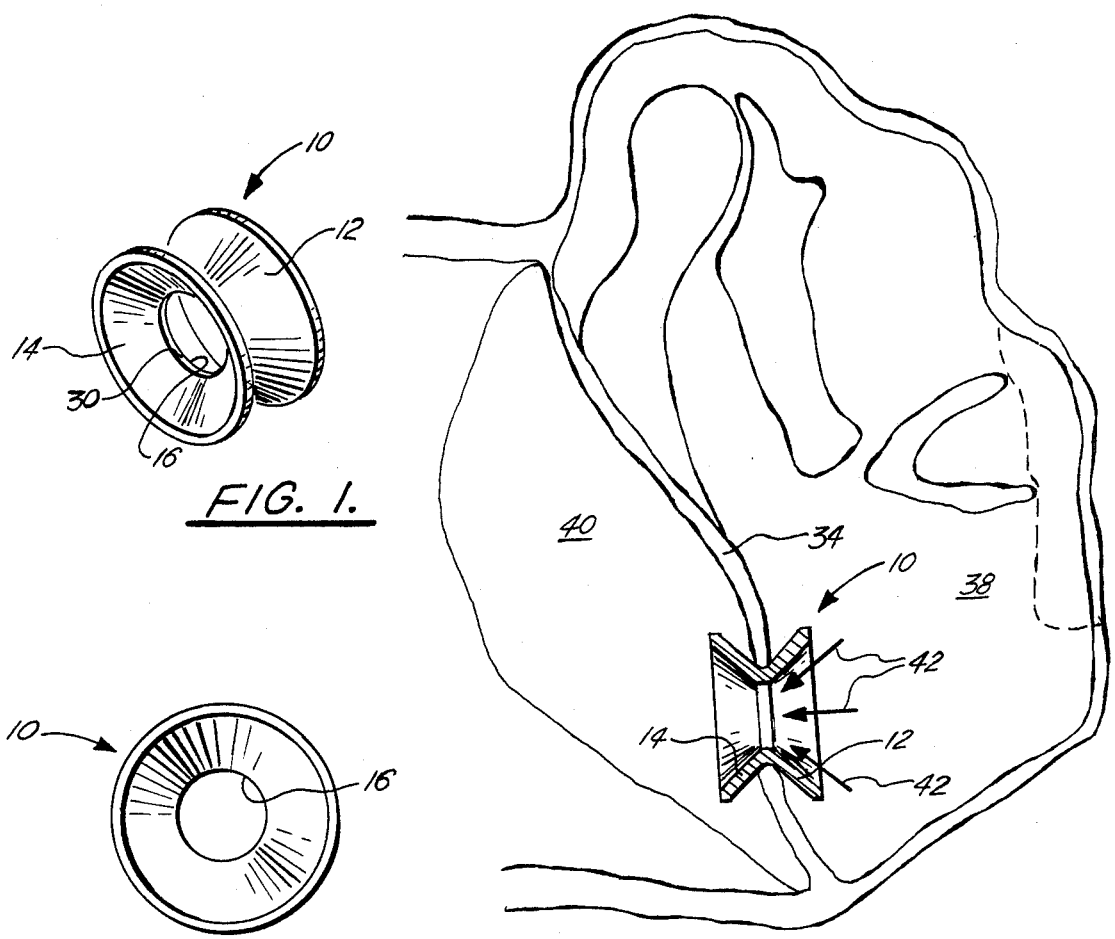
FIG. 1.
FIG. 2.
FIG. 3.
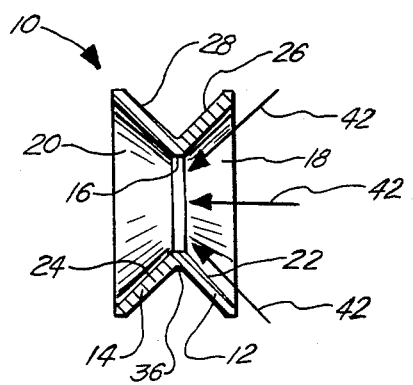
FIG. 4.

V-SHAPED EAR VENTILATION TUBE

FIELD OF THE INVENTION

This invention relates to ventilation or drain tubes that are surgically inserted in the tympanic membrane or eardrum, which are useful for equalizing pressure between the middle ear and outer ear and for draining fluid from the middle ear. More particularly, the invention relates to a vent tube that provides better fluid flow characteristics and is more resistant to clogging than known tubes.

BACKGROUND OF THE INVENTION

The typical remedy for middle ear effusion is a myringotomy surgical procedure that involves surgically forming a slit in the eardrum to relieve a buildup or reduction of pressure in the middle ear cavity. A variety of ear ventilation tubes for insertion into such a slit have been introduced over the years. Such tubes attempt to maintain an opening for a sufficient period of time following surgery to allow pressure to equalize between the middle and the outer ears or to drain fluids from the middle ear.

Vent tubes have been developed with any number of shapes that promote, for example, ease of insertion or removal, resistance to clogging and one-way flow of fluids. However, although these tubes utilize any number of shapes and design variations, most of them maintain a uniform diameter center opening or lumen for conveying fluid from the middle ear into the ventilation tube.

It has been found that conventional vent tubes which have lumen diameters ranging from about 0.75 to 1.5 millimeters have a tendency to clog over time and to impede free flow of fluid when drainage is required. Because of the small size of the tympanic membrane and the risk of leaving a permanent perforation, there is a practical design limitation on the size of the lumen. A diameter found to be acceptable is about 1.27 millimeters.

A tube manufactured by Xomed, Inc., Product No. 10-20000, is known, which has a tube body with a conical shape and a lumen that increases in diameter in a direction away from the outer side of the eardrum. The Xomed tube is connected to the eardrum by means of a flange attached to the smaller diameter end of the tube body, the flange being located on the middle ear side of the eardrum for holding the tube in place. The Xomed tube is thus positioned in the eardrum with the small diameter end of the lumen exposed to the middle ear through the flange. While the Xomed tube appears to have the advantages of a cone-shaped lumen that expands on the outer ear side of the eardrum, it is believed that there are disadvantages in flow characteristics of the highly viscous middle ear fluids to having a narrow lumen opening facing the middle ear.

SUMMARY OF THE INVENTION

The problems mentioned above have been solved in accordance with the present invention by forming a vent tube with a lumen of a relatively small or standard diameter in the center which flares outwardly toward both the middle ear and the outer ear ends. The exterior of the ventilation tube that engages the eardrum is formed in a V-shape with the focus of the V in the center of the ventilation tube.

By providing a vent tube with a lumen of this configuration, the cylindrical surface area of the lumen is decreased over 90%. It is believed that by decreasing the cylindrical surface area of the lumen, fluid draining into the vent tube and tissue growth on the medial side have a reduced tendency to clog the lumen. The flared portion of the lumen placed in the middle ear tends to reduce the severity of the corners about which the viscous fluid within the middle ear must pass. The increased diameter of the inner flare also minimizes the restricted flow length in which effusion from the middle ear can plug the lumen. A flare on the outer ear end of the ventilation tube decreases the surface tension and resistance to flow of fluids including air, thus significantly enhancing the flow characteristics of the vent tube.

By providing an outer surface having a V-shaped configuration, the ventilation tube can be more easily inserted into a slit in the eardrum than a conventional design with a perpendicular flange. The ventilation tube tends to center itself in the plane of the eardrum. The eardrum is in effect wedged between the flared ends. Accordingly, the ventilation tube of the instant invention enhances fluid flow and air ventilation and tends to be retained in the eardrum yielding a longer service life.

DESCRIPTION OF THE DRAWINGS

A better understanding of the invention can be obtained when the detailed description of the preferred embodiment set forth below is considered in conjunction with the appended drawings, in which:

FIG. 1 illustrates a perspective view of a ventilating tube of the instant invention;

FIG. 2 is a front plan view of the ventilating tube of FIG. 1;

FIG. 3 is a cross-section view of middle ear, outer ear and eardrum illustrating a ventilating tube mounted in the eardrum;

FIG. 4 is a side cross-section view of the ventilating tube of FIGS. 1 and 2.

DETAILED DESCRIPTION OF THE INVENTION

Referring to FIG. 1, an ear ventilation tube for insertion in a slit in the tympanic membrane of the ear is generally designated by reference numeral 10. The ventilation tube 10 is formed by a first tapered body portion 12 and a second tapered body portion 14 joined at their narrow ends. The body portions 12, 14 are preferably in the form of truncated cones joined at their narrow ends. An opening or lumen 16 with a first end 18 and second end 20 (see FIG. 4) is formed through the center of the joined body portions 12, 14 to allow fluid to drain and pressure to equalize between a middle ear 38 and an outer ear 40 (see FIG. 3).

The first and second body portions 12, 14 have inner surfaces 22, 24 respectively, and outer surfaces 26, 28 respectively. A cylindrical surface 30 is formed where the inner frusto-conical or tapered flange surfaces 22, 24 join so as to form a constricted portion in the opening 16. It is preferred that the length of cylindrical surface 30 be as short as possible, preferably less than about 0.5 millimeters in length, in order to reduce the restricted flow length of opening 16. The lumen or opening 16 in the ventilation tube 10 is thus formed by inner surfaces 22, 24 and cylindrical surface 30. With this design, the cylindrical surface area of the lumen is reduced by over 90% in comparison to conventional vent tubes.

The outer surfaces 26, 28 of flanges 12, 14 are adapted to engage a tympanic membrane or eardrum 34 (see FIG. 3). The outer surfaces 26, 28 taper to join at a narrow diameter or outer constricted portion 36 for forming a V-shaped outer body surface. The outer surfaces 26, 28 are tapered in order to urge the eardrum 34 toward restriction 36 when the ventilation tube 10 is mounted in the eardrum 34 as shown in FIG. 3. The constricted portion of the lumen 16 is generally situated in the center of the cross-section of the ventilation tube 10 as shown in FIG. 3 and 4 so that the eardrum 36 has less tendency to slip off the outer surfaces 26, 28. The opposed tapered nature of outer surfaces 26, 28 further tends to wedge the eardrum between them for holding the ventilation tube in place.

The decreasing diameter of the opening 16 from both ends 18, 20 toward the center of the lumen 16 performs an important function. When the ventilation tube 10 is implanted in the eardrum 34 as shown in FIG. 3, the decreasing and then increasing diameters of the opening 16 facilitate air ventilation and the flow of fluid trapped in the middle ear 38 to the outer ear 40. Fluid flows in the direction shown by arrows 42 in FIGS. 3 and 4. As they pass through the opening 16, fluid and other particles in the inner ear 38 first enter the large diameter of the first end 18 of the opening 16 formed by the first body portion 14.

The relatively large diameter of the first end 18 of the opening 16 facilitates the flow of fluid from the middle ear 38 and guides the fluid toward the constricted portion of the lumen 16. As the fluid flows through the lumen 16, the interior surface 22 of the first body portion 12 gradually focuses the fluid into the constricted portion of the lumen 16, thereby reducing the possibility of fluid particles hanging up on sharp or squared corners and reducing the effect of hydraulic friction created by such sharp corners. The short cylindrical surface 30 should help reduce clogging because the short lumen length should reduce accumulation of viscous fluid in the lumen 16. In addition, it is believed that the short lumen length enhances removal of any dried fluid or wax from the lumen 16 in comparison to conventional tubes.

The flared inner body portion 12 also is believed to diminish the possibility of tissue from the tympanic membrane clogging the lumen 16. For vent tubes of the type described, tissue growth over the outer surface of the tube has been known to grow over and clog the vent tube opening. However, when the inner opening is as large as that shown in FIG. 1-4, even when there is tissue growth over the outer surface of the tube and part of the lumen 16, the inner end of the luemn 16 is large enough that it will not clog as easily.

Flow through the ventilation tube 10 further enhanced by the increasing diameter of the inner surface 24 of the second body portion 14. It has been found that the flow of fluid through an element such as the ventilation tube 10 is inhibited by surface tension of a fluid meniscus that forms at the outer end of an opening. The surface tension creates back pressure that resists the flow of fluid, thereby increasing the fluid pressure that can build up in the middle ear 38. Increased fluid pressure can cause damage and irritation in the middle ear.

The amount of back pressure created by the meniscus is inversely proportional to the radius of the meniscus, which is determined by the diameter of the outer or downstream opening. Therefore, for the ventilation tube 10, the larger the size of the outer end 20 of the opening 16, the smaller the back pressure that can build and the greater the fluid flow at lower fluid pressures.

Opening 16 should be of sufficient size to allow fluid from the inner ear to pass through the ventilation tube 10, without significant risk of a permanent perforation in the tympanic membrane. The optimum opening 16 is generally considered to range from about 0.75 to 1.5 millimeters in diameter. The diameters of the first and second body portions 12, 14 at their ends 18 and 20 are generally equal and are preferably about 3 mm.

The ventilation tube 10 can be formed of a variety of materials, Metallic materials such as titanium or stainless steel are preferred because they provide smoother surface finishes that tend to discourage tissue growth and reduce the risk of lumen blockage. It should further be noted that while the surfaces 22, 24 and 26, 28 are illustrated as truncated cones with conical surfaces, it is to be understood that the inner surfaces 22, 24 and outer surfaces 26, 28 may also be exponentially or hyperbolically curved, or otherwise shaped, in accordance with the present invention.

The foregoing disclosure and description of the invention are intended to be illustrative and explanatory thereof, and various changes in size, shape and materials as well as in the details of the illustrated construction may be made without departing from the spirit of the invention.

What is claimed is:

1. An ear ventilation tube adapted for insertion in a slit formed in the tympanic membrance portion of a patient's ear for communicating the middle and outer ears, comprising:
    (a) a hollow body formed of a biocompatible material having a fluid flow bore therethrough with inner and outer ends, the bore including a constricted portion that is at least as large in diameter as the minimum size that allows fluid in the middle ear to flow from the middle ear through the bore, the bore including inner and outer portions, each being conical is shape and gradually expanding in size in inner and outer respective directions away from the constructed portion;
    (b) the hollow body further including an outer surface adapted to engage and maintain the tube in the slit in the tympanic membrane.

2. The ventilation tube of claim 1, wherein the constricted portion is formed about mid-way between the inner and outer ends.

3. The ventilation tube of claim 1, wherein the opening is frusto-conical in shape from the constricted portion to the inner and outer ends.

4. The ventilation tube of claim 1, wherein the constricted portion includes a short cylindrical portion.

5. The ventilation tube of claim 1, wherein the outer surface of the hollow body has a narrow central portion which tapers to hollow body end portions of larger size in order to facilitate centering and retention of the ventilating tube in the slit in the tympanic membrane.

* * * * *